United States Patent
Koester

(10) Patent No.: US 8,617,066 B2
(45) Date of Patent: Dec. 31, 2013

(54) AUTOMATED INTERACTIVE DRUG TESTING SYSTEM

(76) Inventor: Danny P. Koester, Evansville, IN (US)

(*) Notice: Subject to any disclaimer, the term of this patent is extended or adjusted under 35 U.S.C. 154(b) by 404 days.

(21) Appl. No.: 12/928,412

(22) Filed: Dec. 10, 2010

(65) Prior Publication Data

US 2011/0144454 A1 Jun. 16, 2011

Related U.S. Application Data

(60) Provisional application No. 61/284,052, filed on Dec. 11, 2009.

(51) Int. Cl.
*A61B 5/00* (2006.01)

(52) U.S. Cl.
USPC ........................................................ 600/300

(58) Field of Classification Search
None
See application file for complete search history.

(56) References Cited

U.S. PATENT DOCUMENTS

| | | | |
|---|---|---|---|
| 8,038,614 B2 * | 10/2011 | Gobeyn et al. | 600/300 |
| 8,038,615 B2 * | 10/2011 | Gobeyn et al. | 600/300 |
| 8,062,220 B2 * | 11/2011 | Kurtz et al. | 600/301 |
| 2006/0111620 A1 * | 5/2006 | Squilla et al. | 600/300 |
| 2006/0173267 A1 * | 8/2006 | Chiang et al. | 600/407 |
| 2007/0073113 A1 * | 3/2007 | Squilla et al. | 600/300 |
| 2008/0199407 A1 * | 8/2008 | Slater et al. | 424/10.3 |
| 2008/0242949 A1 * | 10/2008 | Jung et al. | 600/300 |
| 2008/0242950 A1 * | 10/2008 | Jung et al. | 600/300 |
| 2008/0243005 A1 * | 10/2008 | Jung et al. | 600/481 |
| 2008/0292151 A1 * | 11/2008 | Kurtz et al. | 382/128 |
| 2008/0294012 A1 * | 11/2008 | Kurtz et al. | 600/300 |
| 2009/0012820 A1 * | 1/2009 | Bishop et al. | 705/3 |

OTHER PUBLICATIONS

Kidwell et al. "Testing for drugs of abuse in saliva and sweat" Journal of Chromatography B, 713 (1998) 111-135.*
Johnson et al. "How to spot illicit drug abuse in your patients" vol. 10/No. 4/Oct. 1, 1999/ Postgraduate Medicine.*

* cited by examiner

*Primary Examiner* — Bill Thomson
*Assistant Examiner* — Shirley Jian
(74) *Attorney, Agent, or Firm* — Gary K. Price

(57) ABSTRACT

An automated interactive drug testing system designed for testing for substance abuse that provides an immediate test result by visual analysis. The system includes at least one remote device and a central computer. Each remote device as well as the central computer include means for receiving a video feed over a network connection such that a testing subject located at a remote device can use its video camera to bi-directionally communicate with a person located at the central computer. In application, the testing subject faces the video camera so that the operator at the central computer can witness the testing and testing results. Preferably, the testing can include an eye scan and a saliva swab drug test. It is important for purposes of testing integrity, that during the entire testing process, the test specimen is never removed from view of the camera and the operator stationed at the central computer such that the operator at the central computer can view the testing samples to determine whether the test is negative or non-negative.

14 Claims, 1 Drawing Sheet

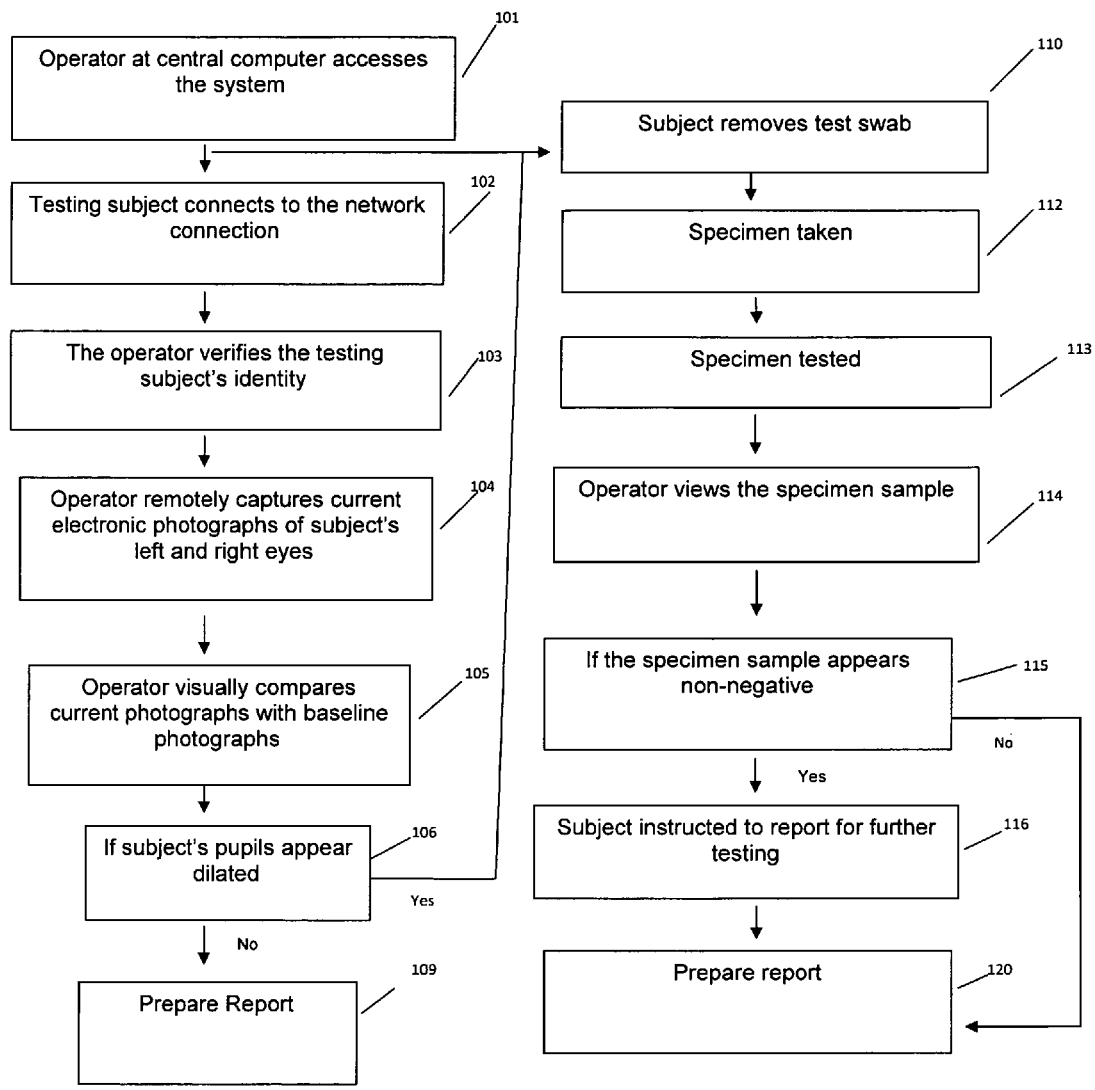

AUTOMATED INTERACTIVE DRUG TESTING SYSTEM

CROSS REFERENCES TO RELATED APPLICATIONS

U.S. Provisional Application for Patent No. 61/284,052, filed Dec. 11, 2009, with title "Automated Interactive Drug Testing System" which is hereby incorporated by reference. Applicant claim priority pursuant to 35 U.S.C. Par. 119(e)(i).

STATEMENT AS TO RIGHTS TO INVENTIONS MADE UNDER FEDERALLY SPONSORED RESEARCH AND DEVELOPMENT

Not Applicable.

BACKGROUND OF THE INVENTION

1. Field of the Invention

The invention relates generally to testing a person for presence of a selected substance, and more specifically to an automated system for testing for selected drugs that includes an immediate test result by visual analysis using video conferencing technology between a remote device and a central computer.

2. Brief Description of Prior Art

Employers today often require perspective employees to undergo pre-employment drug screening, to test for use of selected illegal drugs. Testing for drugs is done not only to ensure that an employer is hiring employees whose work will not be affected by drug use, but also to screen for drug use in other environments. For example, selected employees in jobs with a high degree of responsibility may be regularly screened for drugs, such as truck drivers being screened to ensure they are not using drugs while driving and law enforcement officers being screened for drugs to ensure their actions while working are not affected by drug use. Further, those undergoing drug use rehabilitation may undergo regular if not daily drug tests to ensure that they are no longer using drugs.

Typically, a perspective employee or other test subject is asked to travel to a controlled environment such as a medical facility or laboratory for drug screening. The employer for example must then allow the employee time off work in order to travel and take the drug test, and then must wait for results to be sent back, and also must undergo the expense of transportation and laboratory testing for each subject tested for drugs. Persons on rehabilitation programs are required to regularly "report" to controlled areas for drug screening which is inconvenient at best, and often difficult due to transportation restraints and the like.

What is needed is an inexpensive, efficient and reliable means to undergo drug testing that will provide an immediate indicator of whether the test subject has used drugs recently, and is a valid indicator of drug use. What is further needed is such a drug testing method that avoids the expense and inconvenience of requiring the test subject to travel to an off-site environment.

As will be seen from the subsequent description, the preferred embodiments of the present invention overcome shortcomings of the prior art.

SUMMARY OF THE INVENTION

An automated interactive drug testing system designed for testing for substance abuse that provides an immediate test result by visual analysis. The system includes at least one remote device that is connected to a network connection such as the Internet for permitting a testing subject to connect with a central computer of the system. Each device as well as the central computer include video conferencing equipment. By receiving a video feed over a network connection like a hard-wire or wireless Internet connection, a testing subject located at a remote device can use its video camera to bi-directionally communicate with a person located at the central computer by audio and video.

In application, an operator at the central computer accesses the automated drug testing system and, the testing subject connects to the Internet for example, from the remote device. The operator instructs the subject to place its left eye directly in front of the camera. Once the subject's left eye is in clear view, the operator can remotely capture a current electronic photograph of the subject's left eye. The procedure is then repeated in order to obtain a current electronic photograph of the subject's right eye. The operator then visually compares the current electronic photographs of the subject's left and right eyes with baseline electronic photographs taken of the subject's left and right eyes at the time of the subject's enrollment into the system. If after making the visual comparison the operator determines that the pupils in the current electronic photographs appear dilated or, the subject's eyes in the current electronic photographs appear bloodshot, then the subject will be instructed to begin the swab test. If however, after making the visual comparison the operator determines that the subject's pupils shown in the current electronic photographs appear normal, then the testing is complete and a report is generated and reported to the client.

Next, one test swab is removed from a sealed pack immediately prior to use and is preferably wiped under the testing subject's tongue for approximately 15 seconds. The swab is tested which may include inserting the swab into a swab holder or cartridge and/or adding a controlled fluid to the test swab. As is known in the art, the saliva sample can be visually used to indicate whether the screening test has been successfully run. The person at the central computer views the testing sample to determine whether the test is negative or non-negative. It is critical that during the entire testing session, the testing subject is facing the video camera so that the person at the central computer can witness the sampling and testing of the sampling.

BRIEF DESCRIPTION OF THE DRAWINGS

FIG. 1 shows a flow chart of an automated interactive drug testing system, consistent with an embodiment of the present invention.

DESCRIPTION OF THE PREFERRED EMBODIMENT

In accordance with the present invention, an automated interactive drug testing system is disclosed. The invention relates to testing subjects for selected substances such as drugs of abuse, and a method for inexpensively electronically testing, managing, and reporting the related data. In the broadest context, the automated drug testing system of the present invention consists of components configured and correlated with respect to each other so as to attain the desired objective.

In the preferred embodiment, at least one remote device is connected to a network connection such as the Internet for permitting a test subject to communicate with a central computer of the system. In other embodiments, other means of electronic communication may be used.

In application, the test subject must first personally enroll in the system before using. When enrolling with the system, the test subject may provide a profile that can include the subject's name, and can also include the subject's address, telephone number, and so forth. In addition, the system requires that two (2) electronic photographs be taken and stored in the subject's profile. The first electronic photograph is of the subject's left eye, and the second electronic photograph is of the subject's right eye. As will be understood, these electronic photographs of the subject's left and right eyes, at time of enrollment, establishes a baseline for future drug testing. In addition, the system requires a third electronic photograph be taken and stored in the subject's profile. The third electronic photograph is a full, frontal facial of the testing subject.

The test subject's profile is stored in the central computer. In application, one the test subject is in communications with the central computer, in the preferred embodiment, the test subject is allowed access to the system and testing by looking directly at the imaging device so that the operator at the central computer can compare the test subject's full, frontal facial with the full, frontal facial electronic photograph stored with the subject's profile. In the alternative, the test subject can be allowed access to the system by entering its name from the remote device or, the system may further assign a unique PIN number to the subject and access is granted by entering its assigned PIN number.

Each remote device as well as the central computer include an "imaging device" tethered (or connected hard-wired or wireless). The "imaging device" means equipment for conducting a "video call" where the remote device and central computer are connected to the network connection. In the preferred embodiment, the imagining device is a web camera, video conferencing device, or video device. As should be understood, by receiving a video feed over the network connection, a testing subject located at a remote device can use its video camera to bi-directionally communicate with a person located at the central computer by audio and video.

An example of various steps involved in testing a subject for illegal drug use, and the steps required of the present invention, is illustrated in the flow chart of FIG. 1. Although the blocks of the flow chart are discussed and numbered in a certain order, they need not necessarily be performed in that order.

At step 101, an operator at the central computer logs into or accesses the automated drug testing system. The central computer is connected to the network connection, such as the Internet.

At step 102, the testing subject connects to the network connection and accesses communication with the system from the remote input device as earlier described. In the preferred embodiment, the test subject is allowed access to the system and testing by looking directly at the remote imaging device such that the operator can visually compare the testing subject's current full, frontal facial with the full, frontal facial electronic photograph in the subject's profile. Once the identity of the testing subject is verified at 103, the testing subject will then be in communication with the automated drug testing system.

As previously discussed, once the identity of the testing subject is verified at step 103, the operator, stationed at the central computer, and the testing subject in communication with the system, will then by-directionally communicate with one another by audio and video.

Eye Scan

At step 104, the automated drug testing system initiates the eye scan test. The operator instructs the subject to place its left eye directly in front of the lens of the imaging device or camera. Once the subject's left eye is in clear view, the operator can remotely capture a current electronic photograph of the subject's left eye. The procedure is then repeated in order to obtain a current electronic photograph of the subject's right eye.

At step 105, the operator visually compares the current electronic photographs of the subject's left and right eyes with the baseline electronic photographs taken at the time of the subject's enrollment.

The eye scan test as described will assist in determining if the subject is currently impaired. For example, one of the symptoms with use of methamphetamines is dilated pupils and blurred vision; one of the symptoms for cocaine is dilated pupils; one of the symptoms for LSD (acid) is dilated pupils; and, one of the symptoms for marijuana is blood shot red eyes that are squinty. While the eye scan test as described will assist in determining if the subject is currently impaired, the eye test alone will not conclusively determine if impairment is caused by drugs, alcohol, lack of sleep or other causes.

At step 106, if after making the visual comparison in step 105, the operator determines that the pupils in the current electronic photographs appear dilated when compared with the test subject's baseline electronic photographs or, the subject's eyes in the current electronic photographs appear blood shot, then the subject will be instructed to begin the Swab Test.

At step 107, if after making the visual comparison in step 105, the operator determines that the subject's pupils shown in the current electronic photographs appear normal, then the testing is complete and a report 109 is generated and reported to the client at 120.

Swab Test

At 110, one test swab is removed from a sealed pack immediately prior to use. The swab should be removed from the pack by the person (testing subject) whose saliva is to be tested, and is preferably wiped under the testing subject's tongue for approximately 15 seconds at 112. It is important to note that the sample is taken from the subject while the subject faces the imaging device or camera and therefore all acts by the testing subject can be witnessed by the operator stationed at the central computer via the video call. It is further important to note that for purposes of testing integrity, during the entire testing session, the testing sample is never removed from view of the camera and the operator stationed at the central computer. As such, while the sample is being taken and once the sample is collected from the testing subject, the sample remains in front of the camera at 112.

The swab is tested at 113 which may include the testing subject inserting the swab into a swab holder or cartridge and/or the testing subject adding a controlled fluid to the test swab. As is known in the art, the saliva sample can be visually used to indicate whether the screening test has been successfully run. Again, it is important to note that for purposes of testing integrity, during the entire process discussed at 113, the test swab and swab holder or cartridge are never removed from view of the camera and the operator stationed at the central computer. As such, while the swab is being tested at 113, the testing swab process remains in front of the camera.

If at any time during the testing procedure the testing sample is removed from the operator's view, the operator will immediately instruct the test subject to re-start the swab test procedure at step 110.

At 114, the operator at the central computer views the test swab sample. At step 115, if after viewing the test sample, the operator determines the test is non-negative, the results are then reported to the client at 120 and at 116, the testing subject is instructed to report to the client within a short period of time for example, within twenty-four (24) hours, for further testing.

The invention described herein includes a method of performing drug testing to determine whether a sample contains specific substances of abuse. The screening method provides an immediate test result by visual analysis, and the result and user data are entered of record. Still further, it will be appreciated that embodiments of the disclosed invention provide a versatile system and method for implementing drug screening programs designed for testing for substance abuse. The disclosed system offers important new and useful results in that it allows an entity to operate many remote stations at various locations, without having to have the remote stations networked together.

Although specific embodiments have been illustrated and described herein, it will be appreciated by those of ordinary skill in the art that any arrangement which is calculated to achieve the same purpose may be substituted for the specific embodiments shown.

For example, rather than the screening test at 110 using a test swab as described, other testing specimens from the subject can be used for drug testing such as, but not limited to, hair samplings, sampling of the subject's skin may achieve the same purpose as the test swab. As such, this application is intended to cover any adaptations or variations of the invention.

Thus the scope of the invention should be determined by the appended claims in the formal application and their legal equivalence, rather than by these examples given.

I claim:

1. A method for testing for substance abuse that provides an immediate test result by visual analysis, said method comprising the following steps:
   receiving a video feed over a network connection between a testing subject at a remote device and an operator at a central computer, each said remote device and central computer includes an imaging device to bi-directionally communicate, and wherein said testing subject is facing the imaging device at the remote device during the testing method so that the operator at the central computer can witness each step of the testing;
   performing an eye scan test comprising the following steps:
   capturing a current electronic photograph of the testing subject's right eye,
   capturing a current electronic photograph of the testing subject's left eye,
   visually comparing the current electronic photograph of the testing subject's right eye with a baseline electronic photograph of the subject's right eye stored in the central computer, wherein said baseline electronic photograph of the subject's right eye is stored at time of the subject's enrollment,
   visually comparing the current electronic photograph of the testing subject's left eye with a baseline electronic photograph of the subject's left eye stored in the central computer, wherein said baseline electronic photograph of the subject's left eye is stored at the time of the subject's enrollment,
   determining from said visual comparisons whether the eye scan test is negative or non-negative and in the event said eye scan test is negative then reporting the results of the eye scan test; and, in the event said eye scan test is non-negative then performing a swab test comprising the following steps in the sequence set forth:
   removing one test swab, said test swab including a swab holder having a controlled fluid,
   wiping said test swab under the testing subject's tongue to obtain a sampling,
   inserting the test swab with the sampling into the swab holder,
   said operator viewing said sampling from the imaging device at the central computer to determine whether the swab test is negative or non-negative,
   reporting the results from the swab test.

2. The method of claim 1, wherein the step of reporting the results from the eye scan test includes the step of generating a report indicating the test results and reporting the results to a client.

3. The method of claim 1, wherein the step of reporting the results from the swab test includes the step of generating a report indicating the test results and reporting the results to a client.

4. A method for testing for substance abuse that provides an immediate test result by visual analysis, said method comprising the following steps:
   receiving a video feed over a network connection between a testing subject at a remote device and an operator at a central computer, each said remote device and central computer including a video camera to bi-directionally communicate, and wherein said testing subject is facing the video camera at the remote device during the testing method so that the operator at the central computer can witness each step of the testing,
   verifying the identity of the testing subject,
   performing a first substance abuse test comprising the following steps:
   taking an electronic photograph of the testing subject's right eye,
   taking an electronic photograph of the testing subject's left eye,
   retrieving a baseline electronic photograph of the subject's right eye stored on the central computer and comparing the electronic photograph of the testing subject's right eye with the baseline electronic photograph of the subject's right eye, wherein said baseline electronic photograph of the subject's right eye is stored at the time of the subject's enrollment,
   retrieving a baseline electronic photograph of the subject's left eye stored on the central computer and comparing the electronic photograph of the testing subject's left eye with the baseline electronic photograph of the subject's left eye, wherein said baseline electronic photograph of the subject's left eye is stored at the time of the subject's enrollment,
   determining whether the first substance abuse test is negative or non-negative based upon, the above comparing steps,
   performing a second substance abuse test comprising the following steps:
   collecting a specimen, wherein said specimen is saliva taken from under the testing subject's tongue using a test swab and a swab holder having controlled fluid that reacts to said test swab,
   testing the specimen for substance abuse, wherein during said testing steps the testing subject is facing the video camera at the remote device and the operator is viewing said specimen from the video camera at the central computer,
   determining whether said specimen is negative or non-negative, reporting the results from the first and second substance abuse tests.

5. The method of claim 4, wherein the step of reporting the results includes the step of generating a report indicating the test results and reporting the results to a client.

6. The method of claim 5, further including the step of the testing subject setting up a user profile that includes said baseline electronic photograph of the subject's right eye and said baseline electronic photograph of the subject's left eye.

7. The method of claim 6, wherein said user profile further includes an electronic photograph of the subject's full, frontal facial.

8. The method of claim 7, wherein the above verifying step includes comparing the testing subject's current full, frontal facial with the full, frontal facial electronic photograph in the subject's profile.

9. A method for testing for substance abuse that provides an immediate test result by visual analysis, said method comprising:

receiving a video feed over a network connection between a testing subject at a remote device and an operator at a central computer, each said remote device and central computer includes an imaging device to bi-directionally communicate, and wherein said testing subject is facing the imaging device at the remote device during the testing method so that the operator at the central computer can witness each step of the testing, verifying the identity of the testing subject, removing one test swab, wiping said test swab under the testing subject's tongue to obtain a sampling, inserting the test swab with the sampling into a holder having a controlled fluid that reacts with said test swab, said operator viewing said sampling from the imaging device at the central computer to determine whether the test is negative or non-negative, reporting the results from the swab test.

10. The method of claim 9, includes performing an eye test before the removing one test swab step, said eye test comprising the steps of:

taking an electronic photograph of the testing subject's right eye, taking an electronic photograph of the testing subject's left eye, retrieving a baseline electronic photograph of the subject's right eye stored on the central computer and comparing the electronic photograph of the testing subject's right eye with the baseline electronic photograph of the subject's right eye, retrieving a baseline electronic photograph of the subjects left eye stored on the central computer and comparing the electronic photograph of the testing subject's left eye with the baseline electronic photograph of the subject's left eye, determining whether the eye test is negative or non-negative based upon the above comparing steps.

11. The method of claim 10, further including the step of the testing subject setting up a user profile.

12. The method of claim 11, wherein said user profile includes said baseline electronic photograph of the subject's right eye and said baseline electronic photograph of the subject's left eye.

13. The method of claim 12, wherein said user profile further includes an electronic photograph of the subject's full, frontal facial.

14. The method of claim 13, wherein the above verifying step includes comparing the testing subject's current full, frontal facial with the full, frontal facial electronic photograph in the subject's profile.

\* \* \* \* \*